United States Patent
Sarstedt

[19]

[11] Patent Number: 5,997,275
[45] Date of Patent: Dec. 7, 1999

[54] MOLD FOR MAKING A PART WITH LUGS

[75] Inventor: Walter Sarstedt, Nümbrecht, Germany

[73] Assignee: Sarstedt AG & Co., Numbrecht, Germany

[21] Appl. No.: 08/893,694

[22] Filed: Jul. 11, 1997

[30] Foreign Application Priority Data

Jul. 11, 1996 [DE] Germany .......................... 196 27 948

[51] Int. Cl.⁶ .................................................. B29C 33/42
[52] U.S. Cl. ..................... 425/450.1; 249/119; 425/577; 425/441
[58] Field of Search ................................ 425/450.1, 470, 425/572, 588, DIG. 58, 577, 441; 249/117, 119, 126, 140, 63, 64; 264/297.2, 318, 328.1, 328.8, 334

[56] References Cited

U.S. PATENT DOCUMENTS

| | | | |
|---|---|---|---|
| 1,475,463 | 11/1923 | Weida ...................................... | 264/318 |
| 3,667,636 | 6/1972 | Landen . | |
| 3,735,785 | 5/1973 | Nigro . | |
| 3,840,636 | 10/1974 | Deguchi et al. . | |
| 4,040,595 | 8/1977 | Tecco ...................................... | 425/588 |
| 4,090,837 | 5/1978 | Balevski et al. .......................... | 425/588 |
| 4,556,190 | 12/1985 | Smith ....................................... | 264/318 |
| 4,960,394 | 10/1990 | Marks et al. ............................. | 264/318 |
| 4,969,811 | 11/1990 | Littleton ................................... | 249/64 |
| 4,986,942 | 1/1991 | Irgens et al. ............................. | 264/334 |
| 5,112,556 | 5/1992 | Miller ................................... | 264/328.8 |
| 5,298,208 | 3/1994 | Sibley et al. ............................. | 264/318 |
| 5,472,655 | 12/1995 | Morita ...................................... | 425/588 |
| 5,607,392 | 3/1997 | Kanner . | |
| 5,635,126 | 6/1997 | Nomura et al. .......................... | 264/334 |
| 5,698,149 | 12/1997 | Hinzmann et al. ............... | 425/DIG. 58 |
| 5,716,579 | 2/1998 | Sorensen et al. ........................ | 264/318 |

FOREIGN PATENT DOCUMENTS

| | | |
|---|---|---|
| 0598169 | 5/1994 | European Pat. Off. . |
| 2294041 | 7/1976 | France . |
| 30 49 503 | 7/1982 | Germany . |
| 89 02 945 | 5/1989 | Germany . |
| 3-193322 | 8/1991 | Japan ..................................... 425/588 |
| 2277685 | 11/1994 | United Kingdom . |

OTHER PUBLICATIONS

Rosato et al., Injection Molding Handbook, second edition, pp. 220–226 and 597–601, 1995.

Butler, J., Compression and Transfer Moulding of Plastics, pp. 28–37, 1959.

Whelan, A., Injection Moulding Machines, pp. 221–225, 1984.

"Wann Lohnen Sich Etagenwerkzeuge", R.Bertschi,Wiesbaden; Kunstoffe 86, (1996)5,4 pages.

*Primary Examiner*—Jill L. Heitbrink
*Attorney, Agent, or Firm*—Herbert Dubno; Andrew Wilford

[57] ABSTRACT

A molding apparatus has a fixed mold part having a pair of flat side faces and formed on each face with a plurality of laterally open half cavities and respective movable mold parts each having a side face juxtaposed with a respective fixed-part side face and displaceable transversely into and out of a molding position with the movable-part side face flatly engaging the respective fixed-part side face of the stationary mold part. Each movable mold part is formed with a plurality of half cavities forming full mold cavities with the half cavities of the respective fixed-part side face in the molding position. Each movable-part half cavity is formed with at least two inwardly open pockets, one of the pockets of each movable-part half cavity being open at the respective movable-part side face and being transversely closed by the respective fixed-part side face.

4 Claims, 1 Drawing Sheet

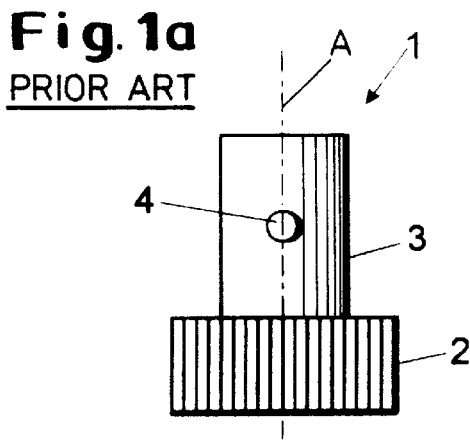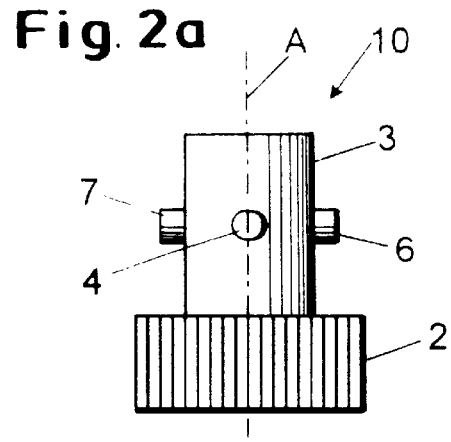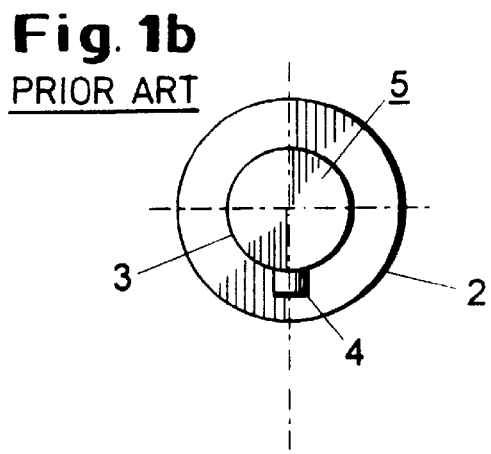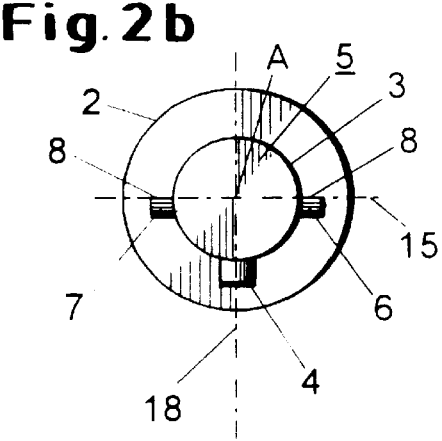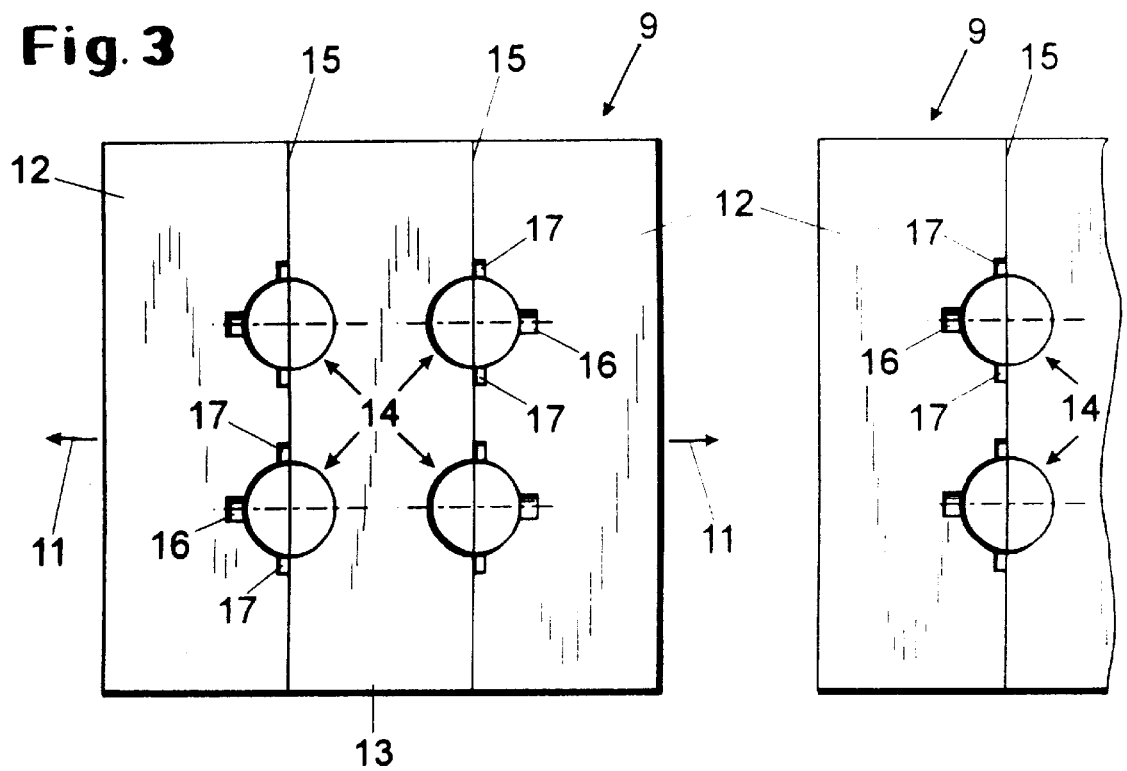

MOLD FOR MAKING A PART WITH LUGS

FIELD OF THE INVENTION

The present invention relates to a molded part. More particularly this invention concerns a molded cap and a mold for making the cap.

BACKGROUND OF THE INVENTION

When producing molded parts, in particularly when they are at least partially hollow, there are substantial problems involved in removing the parts from the mold, that is demolding. These problems are particularly aggravated when the molded part has lateral projections so that it must be produced in a multi-part mold.

This is a particularly problem in making a cap for a blood-drawing kit as described in my U.S. Pat. No. 4,449,539. Such a cap forms a stable connection between the top of a blood vial and a cannula-carrying holder. Such a stable connection is for example desired also when mounting a blood-drawing tube on the device. In such a drawing device a cap is screwed onto the vial, which is provided with a piston, and in turn the cannula-carrying holder is fitted to the cap. To this end the cap has a cylindrical extension whose end wall has a central hole closed by a pierceable and self-sealing membrane. The cannula extends from both sides of its holder and has points at both ends so that as the holder is axially fitted to the cap, the back point is pressed axially through the membrane of the cap. The front point is the actual needle that can be inserted into a vein.

To retain the holder on the cap, the cap is normally provided with a radially projecting cylindrical lug or tab and the holder has an L-shaped groove or slot. The lug moves along an axially extending leg of the groove as the holder is fitted to the cap, and at the end of its travel the holder is twisted to lock the lug in an angularly extending shorter leg of the groove, like a bayonet mount.

It is essential that the holder be solidly secured to the cap. The single mounting lug has, therefore, been found to be inadequate in that it can allow the holder to tip so it has been suggested to provide two or more such lugs for a multipoint connection. In general it is desired to have at least two diametrally opposite lugs to prevent tipping of the holder on the cap, and preferably three to prevent tipping in any direction.

The cap is, however, an item that is mass produced in very large quantities, as such caps are used in large quantities and are discarded after a single use, so it must be made very cheaply. Hence the caps are typically formed in a so-called multi-daylight mold. Such arrangements have a central fixed mold part having a pair of opposite sides each forming with a respective movable mold part a plurality of mold cavities. The single lug can easily be formed by a pocket in the cavity of the movable mold part so that, once the mold is opened, the finished part can be knocked out of the fixed mold half axially, once of course a core element has been withdrawn. Obviously it would be impossible to make a two- or three-lug cap in such a multi-daylight mold since it would be necessary to form some of the lugs in the fixed mold part, making it impossible to knock out the molded pieces without shearing off the lugs in the fixed mold part.

OBJECTS OF THE INVENTION

It is therefore an object of the present invention to provide an improved molded part and method of making same.

Another object is the provision of such an improved molded part and method of making same which overcomes the above-given disadvantages, that is which has more than one lug.

A further object is to provide an improved molding apparatus of the multi-daylight type which can make a multiple-lug cap of the type described above.

SUMMARY OF THE INVENTION

A molding apparatus has according to the invention a fixed mold part having a pair of flat side faces and formed on each face with a plurality of laterally open half cavities and respective movable mold parts each having a side face juxtaposed with a respective fixed-part side face and displaceable transversely into and out of a molding position with the movable-part side face flatly engaging the respective fixed-part side face of the stationary mold part. Each movable mold part is formed with a plurality of half cavities forming full mold cavities with the half cavities of the respective fixed-part side face in the molding position. Each movable-part half cavity is formed with at least two inwardly open pockets, one of the pockets of each movable-part half cavity being open at the respective movable-part side face and being transversely closed by the respective fixed-part side face.

Thus with this system, once the movable parts are pulled away from the fixed part, all the lugs are exposed so the molded cap can be knocked axially out of the fixed part. Thus it is possible to use the highly efficient system of a multi-daylight mold while still producing a fairly complexly shaped workpiece.

The one pockets according to the invention are of semi-cylindrical shape. In addition each movable-part half cavity has two such pockets open at the respective side face. Each movable-part half cavity has a third such pocket of cylindrical shape and open perpendicular to the respective movable-part side face.

The molded part has according to the invention a large-diameter cylindrical and internally threaded collar centered on an axis, a smaller-diameter sleeve extending coaxially and integrally from the collar, a full lug projecting radially from the collar, and a half lug projecting radially from the collar and having a flat side extending in a plane including the axis. Both of the lugs lie to one side of the plane. Normally in accordance with the invention the full lug is cylindrical and the half lug is semicylindrical. In addition another half lug projects radially from the collar and has a flat side lying on the plane. The other half lug is substantially 180° offset from the first-mentioned half lug and substantially 90° offset from the full lug.

BRIEF DESCRIPTION OF THE DRAWING

The above and other objects, features, and advantages will become more readily apparent from the following description, reference being made to the accompanying drawing in which:

FIGS. 1a and 1b are side and top views of a prior-art molded cap according to the invention;

FIGS. 2a and 2b are side and top views of a cap according to the present invention; and FIG. 3 is a small-scale top view of a mold assembly for making the cap according to the invention.

SPECIFIC DESCRIPTION

As seen in FIGS. 1a and 1b a standard cap 1 of the type described in my above-cited patent is centered on an axis A and has an internally threaded and externally knurled large-diameter collar 2 adapted to be screwed onto the end of a blood vial or onto a fitting of a blood-collecting tube. A smaller-diameter and similarly cylindrical sleeve 3 extends coaxially from the collar 2 and has an upper end closed by a pierceable membrane 5 and is adapted to interfit with a cannula holder. A single cylindrical lug 4 extends radially from the sleeve 4 and seats in a bayonet slot in the cannula holder to secure the holder and cap together.

FIGS. 2a and 2b show a cap 10 according to the invention which is identical to the cap 1 except that, in addition to the cylindrical lug 4, it has two semicylindrical lugs 6 and 7 each extending relative to the axis A at a 90° angle to the lug 4. More specifically each such lug 6 and 7 has a flat side 8 lying on a plane 15 including the axis A and perpendicular to a plane 18 bisecting the lug 4 and including the axis A. All the lugs 4, 6, and 7 lie to one side of this plane 15.

Such a cap 10 can be made in a multi-daylight mold 9 of the type shown in FIG. 3, having a fixed center part 13 and a pair of side parts 12 movable toward and away from the fixed part 13 as shown by arrows 11. Each side face of the fixed part 13 forms with the respective movable part 12 two cavities 14 for making the caps 10, there of course being unillustrated core parts movable parallel to the planes for shaping the interiors of the caps 10.

According to the invention the movable parts 12 are formed with subcavities 16 and 17 that form the lugs 4, 6, and 7. The planar side faces of the fixed part 13 therefore form the flats 8 of these lugs 6 and 7. Thus it is possible, once the movable side parts 12 have been retracted and, of course, the unillustrated core parts have been retracted, to knock the finished caps 10 axially out of the cavities 14.

In use the semicylindrical lugs 6 and 7 are as effective as the full-cylindrical lug 4 in holding the cap 10 in a cannula holder. Proper centering is ensured by the full-cylindrical lug 4 and the others guarantee that the holder will not tip on the cap 10.

I claim:

1. A molding apparatus comprising:

a fixed mold part having a planar side face and formed on the face with a laterally open half cavity; and a movable mold part having a planar side face juxtaposed with the fixed-part side face and displaceable laterally into and out of a molding position with the movable-part side face flatly engaging the fixed-part side face of the stationary mold part, the movable part being formed on the respective side face with a respective half cavity forming a full mold cavity with the half cavity of the fixed-part side face in the molding position, the movable-part half cavity being formed with at least two pockets open inwardly into the respective half cavity, one of the pockets of the movable-part half cavity being open at the movable-part side face and being laterally closed by the fixed-part side face in the molding position and the other pocket being open perpendicular to the movable-part side face, whereby when the mold parts are separated a piece molded between them can be knocked out of the fixed part parallel to the respective side face without damage to lugs molded in the pockets.

2. The molding apparatus defined in claim 1 wherein the one pocket is of semicylindrical shape.

3. The molding apparatus defined in claim 2 wherein the movable-part half cavity has two such one pockets open at the respective side face.

4. The molding apparatus defined in claim 3 wherein the other pocket is of cylindrical shape.

* * * * *